Figure 1:
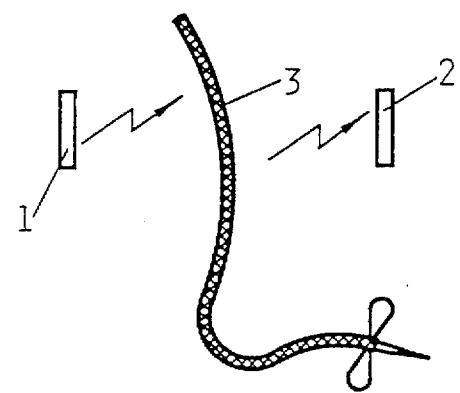

United States Patent [19]
Hemmingsen et al.

[11] Patent Number: 5,741,216
[45] Date of Patent: Apr. 21, 1998

[54] PRESSURE MONITOR

[75] Inventors: Allan Hemmingsen, Espergaerde; Bo Steffensen, Stenloese, both of Denmark

[73] Assignee: Novo Nordisk A/S, Bagsvaerd, Denmark

[21] Appl. No.: 313,183

[22] PCT Filed: Apr. 1, 1993

[86] PCT No.: PCT/DK93/00122

§ 371 Date: Nov. 4, 1994

§ 102(e) Date: Nov. 4, 1994

[87] PCT Pub. No.: WO93/20865

PCT Pub. Date: Oct. 28, 1993

[30] Foreign Application Priority Data

Apr. 10, 1992 [DK] Denmark .................................. 0480/92

[51] Int. Cl.⁶ .................................................. A61B 5/02
[52] U.S. Cl. .................................... 600/488; 128/748
[58] Field of Search ........................... 604/118; 128/748, 128/674, 675, 684

[56] References Cited

U.S. PATENT DOCUMENTS

| | | | |
|---|---|---|---|
| 3,209,596 | 10/1965 | Kelly | 73/401 |
| 4,599,901 | 7/1986 | Hirschfeld | 128/675 X |
| 4,691,708 | 9/1987 | Kane | 128/675 X |
| 4,727,730 | 3/1988 | Boiarski et al. | 128/675 X |
| 4,803,992 | 2/1989 | Lemelson | 128/675 X |
| 4,883,062 | 11/1989 | Nicholson | 128/748 X |
| 5,107,847 | 4/1992 | Knute et al. | 128/675 |
| 5,154,680 | 10/1992 | Drzewiecki et al. | 128/657 X |

FOREIGN PATENT DOCUMENTS

| | | | |
|---|---|---|---|
| 1053723 | 3/1959 | Germany | 128/684 |
| WO 90/07942 | 7/1990 | WIPO . | |

Primary Examiner—Sam Rimell
Attorney, Agent, or Firm—Steve T. Zelson, Esq.

[57] ABSTRACT

The present invention is a pressure monitor for measuring the pressure in a liquid in catheter, comprising a light emitting device, a photosensitive device receiving the light from the light emitting device and transforming the light received into electric signals. The invention also includes a measuring zone. The light transmitted through the measuring zone varies in accordance with the pressure in the catheter.

10 Claims, 3 Drawing Sheets

PRESSURE MONITOR

CROSS-REFERENCE TO RELATED APPLICATIONS

This application is a national stage of PCT/DK93/00122 filed Apr. 1, 1993, filed under 35 USC 371.

The inventions relates to pressure monitors and to be more specific to pressure monitors for measuring the pressure in a catheter.

From WO 90/07942 it is known that the overall correct function of an infusion pump may be supervised by considering the course of the pressure in the outlet catheter during each pumping cycle. It is important that the actual pressure in the very catheter is measured and not just the resistance a piston exerts against movement.

It is the object of the invention to provide a pressure monitor measuring the pressure in the catheter directly.

This is obtained by a monitor comprising a light emitting device and a light measuring device placed opposite each other leaving a space for insertion of a measuring zone of the catheter between these parts, this measuring zone lying downstream of a possible output valve of a pump, and a computer circuit transforming the signals from the light measuring part into signals representative to the pressure.

The light source may be one or more cooperating surface light emitting diodes jointly having a size corresponding to the size of the measuring zone.

Correspondingly, the photo sensitive device may be formed by one or more photo cells working in parallel and jointly having a size corresponding to the size of the light emitting device.

The measuring zone may be a part of the catheter tubing or may be an appendix to the catheter, this appendix forming a manometer tube.

When the manometer tube solution is used, the light measuring device may appropriately be a linear array of mutually independent photocells, this array having a length corresponding to the length of the branch tube. With this embodiment of the light measuring part it can be measured to which extent the infusion liquid rises in the manometer tube.

Catheters for infusion pumps may have the shape of a tubing forming the complete flow path for the liquid to be infused from a reservoir. The pumping function may be obtained by part of the catheter forming a part of a peristaltic pump or being provided with another sort of pumping unit. In the last mentioned case, the manometer tube may be provided in this pumping unit downstream of the outlet valve of this unit. Thereby it is possible to mould the pumping unit with the manometer tube to obtain a more precise manometer tube.

The invention also comprises a catheter provided with a branch tube forming a manometer tube. This branch tube may appropriately be provided near a pump delivering an infusion liquid through the catheter, but downstream in relation to the output valve function of this pump.

A catheter may comprise a pumping unit forming a part of this catheter, and the branch tune may be provided as a bore in this unit.

Figure 2:
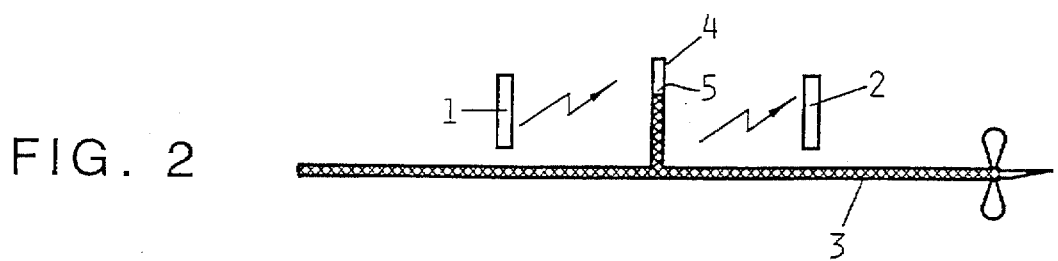
Figure 3:
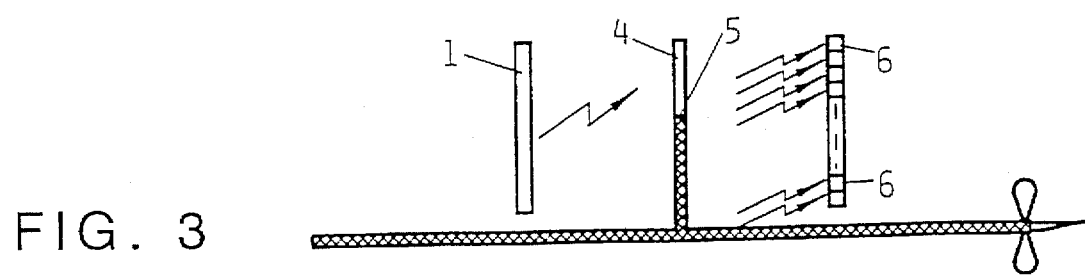

In the following the invention will be described with reference to the drawing, wherein FIG. 1 schematically shows a monitor comprising a light emitting part and a light measuring part with an interjacent measuring zone of a catheter, FIG. 2 schematically shows a monitor as shown in FIG. 1 where the measuring zone of the catheter is provided as an appendix to the catheter, FIG. 3 schematically shows a monitor measuring the level in a manometer tube.

A pressure monitor for measuring the actual pressure in a catheter is shown schematically in FIG. 1. The monitor comprises a light source 1 which may be a light emitting diode, LED, emitting its light from an elongated surface, a photo cell 2 for receiving light on a surface of about the same size and shape as the light diode. The LED and the photo cell are placed opposite each other and spaced so far that room is made for accommodating a measuring zone of a catheter 3.

It has appeared that the light transmission through the liquid filled catheter varies with the internal pressure in the catheter, and consequently an output signal reflecting the pressure variations in the catheter may be obtained from the photo cell. The signal is lead to a calculating unit setting the zero point, when a new catheter is inserted. Advantage is taken of the fact that a measurement of the absolute pressure is not needed, as the monitoring method stated in WO 90/07942 only considers variations in the pressure from one pumping cycle to the other.

Another embodiment of a pressure monitor is shown in FIG. 2. In this embodiment, not the catheter 3 itself but an appendix 4 on this catheter is inserted between the light source 1 and the photo cell 2. The appendix has the shape of a short tube, the bore of which communicates with the clear of the catheter and is closed at the outer end of the appendix. Thereby a manometer tube is provided.

When the catheter is filled with liquid, some air will be trapped in the manometer tube, and a surface 5 separating air and liquid will appear in the manometer tube. When the liquid in the catheter is set under pressure, this surface will be forced further up into the manometer tube. When the manometer tube is placed between the light source 1 and the photo cell 2, the light transmission will be influenced by the varying position of the liquid surface 5, as the transmission properties of the liquid filled part of the manometer tube will be different from the transmission properties of the part filled with air.

FIG. 3 shows an embodiment of a monitor measuring the light transmission perpendicular to a manometer tube. This monitor has a light source 1 as the embodiments according to FIGS. 1 and 2, but instead of one photo cell or more photocells operating in parallel it has an array of photo cells 5, each supplying its own output signal. Thereby it is made possible to read exactly the position of the liquid surface 5, as a distinct difference in transmission may be seen between the cells in the array receiving light from the light source through the air filled part and the cells receiving the light through the liquid filled part of the manometer tube.

When the catheter is filled with unpressurized liquid, the position of the separating surface is noticed and further the end of the appendix may be noticed, as a distinct difference in transmission is also seen between the part of the appendix having an air filled bore and the solid part closing the outer end of the branch tube. Hereafter the position of the separating surface may be read with a precision depending on the number, size, and spacing of the photo cells 6 in the array. Hereby the absolute pressure may be calculated by recognizing the law for confined gasses.

To discriminate between the signals from the photo cells 6 in the array, an output from each cell must lead to the computer. Alternatively, a circuit may be provided in connection with the array to transform the output signal to a sequential signal.

The monitor is intended to be a part of an infusion pump frequently infusing doses of liquid. During each infusion the course of the pressure in the catheter has to be monitored to supervise that the doses are actually infused and no functional errors occur. Consequently, the monitor needs only be activated in connection with the frequent infusion cycles, and power may be saved by turning off the light source between these cycles.

We claim:

1. An apparatus for directly monitoring the pressure of a liquid in a catheter, the apparatus comprising:
   a light emitting device;
   a photo sensitive device spaced from said light emitting device; and
   a catheter having a light transmissible measuring zone, said measuring zone being disposed between said light emitting device and said photo sensitive device;
   wherein said photo sensitive device receives light from said light emitting device transmitted through said measuring zone of said catheter, said photo sensitive device transforms the received light into electric signals reflecting an amount of light transmitted through said measuring zone of said catheter.

2. An apparatus according to claim 1, wherein the light emitting device comprises a number of co-operating surface light emitting diodes jointly having a size corresponding to the measuring zone.

3. An apparatus according to claim 1, wherein the measuring zone is a part of a tubing constituting the catheter.

4. An apparatus according to claim 1, wherein the measuring zone is a branch tube to the catheter, which branch tube has a closed end.

5. An apparatus according to claim 4, wherein the branch tube is provided in a part of a pump provided as an integral part of the catheter, the branch tube being provided downstream in relation to valve means in said part.

6. An apparatus according to claim 1, wherein the photo sensitive device comprises a number of co-operating photocells working in parallel and jointly having a size corresponding to a joint light emitting surface presented by the emitting device.

7. An apparatus according to claim 4, wherein the photo sensitive device is a linear array of mutually independent photo cells.

8. An apparatus according to claim 4, wherein the branch tube is provided near a pump delivering an infusion liquid through the catheter, but downstream in relation to an output of this pump.

9. An apparatus according to claim 4, wherein the branch tube is formed as a bore in a pumping unit forming a part of the catheter.

10. An apparatus according to claim 1, wherein the amount of light transmitted through said measuring zone varies with an internal pressure in said catheter.

* * * * *